United States Patent [19]

Firth

[11] 4,037,605
[45] July 26, 1977

[54] TRACHEOTOMY TUBE
[76] Inventor: Bernard Charles Firth, 114 Grey Street, East Melbourne, Victoria 3002, Australia
[21] Appl. No.: 676,588
[22] Filed: Apr. 13, 1976
[30] Foreign Application Priority Data
    Aug. 14, 1975   United Kingdom ............... 15148/75
    June 19, 1975   United Kingdom ............... 26058/75
[51] Int. Cl.² .......................................... A61M 25/00
[52] U.S. Cl. ................................................. 128/351
[58] Field of Search ..................... 128/348, 351, 208, 5
[56] References Cited
U.S. PATENT DOCUMENTS
  466,004   12/1891   Davis ........................................ 128/5
3,688,774   9/1972   Ariyama ................................ 128/351
3,693,624   9/1972   Shiley et al. ......................... 128/351

FOREIGN PATENT DOCUMENTS
  249,568   12/1969   U.S.S.R. ............................... 128/351

Primary Examiner—Dalton L. Truluck
Attorney, Agent, or Firm—Blanchard, Flynn, Thiel, Boutell & Tanis

[57]           ABSTRACT

A cuffed tracheotomy tube having an aperture in the wall thereof and removable insert means to engage and seal the aperture in an airtight manner. With the insert means in position within the tube to close and seal the aperture and the cuff inflated a patient is ventilated by a ventilator. Upon removal of the insert means the patient can ventilate himself in a normal, natural manner spontaneously through the nose and mouth.

9 Claims, 4 Drawing Figures

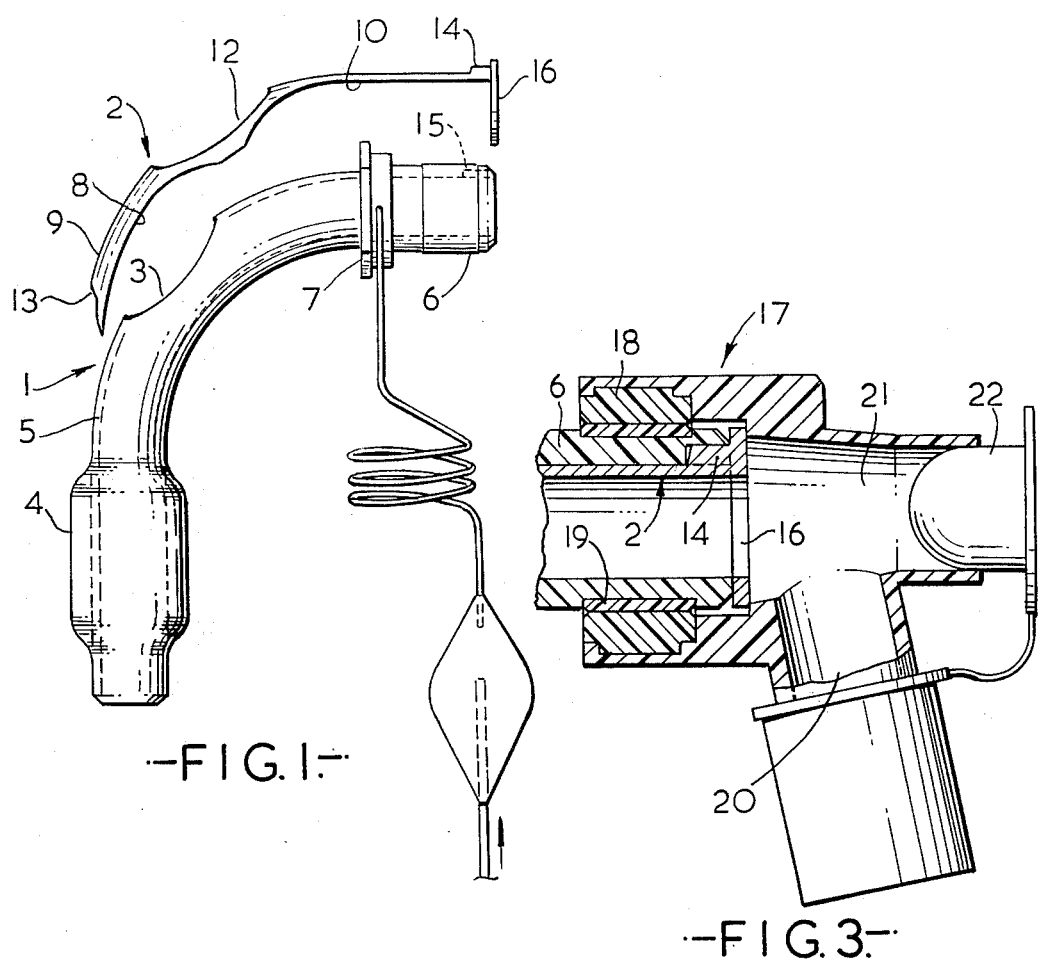
FIG. 1.
FIG. 3.
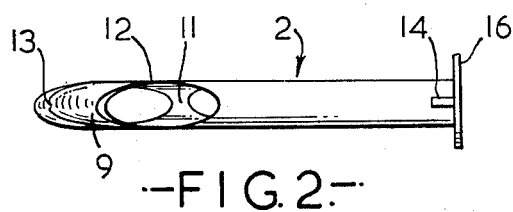
FIG. 2.
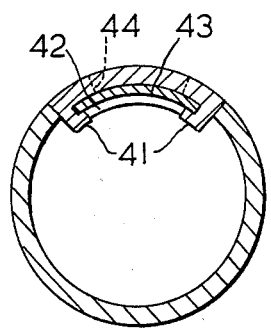
FIG. 4.

TRACHEOTOMY TUBE

FIELD OF THE INVENTION

The present invention concerns a fenestrated, cuffed tracheotomy tube.

BACKGROUND OF THE INVENTION

It is known and accepted practice to insert a cuffed tracheotomy tube into a patient's windpipe through a surgical opening in the neck in order to connect the patient to a ventilator. Upon insertion the cuff, which in effect is a collapsible, closed annular chamber about the end of the tube, in inflated whereby to provide a substantially airtight seal between the tube and the wall of the windpipe. This ensures that incoming air from the ventilator on leaving the tube passes into the lungs and cannot escape and leak away about the exterior of the tube.

Such a known tube is effective but suffers from the disadvantage in that once inserted in position it is impossible for the patient to ventilate himself in the normal, natural manner through the nose and mouth. Usually a patient will be encouraged to leave the ventilator in a progressive manner. Thus the patient will be encouraged to ventilate himself spontaneously for progressively increasing time intervals. This necessitates the removal of the tube to allow the patient to breathe through the mouth and nose and the reinsertion of the tube for reconnection to the ventilator. The repeated removal and reinsertion of the tube can be an uncomfortable and distressing experience for the patient.

The present invention seeks to provide a tracheotomy tube which does not require to be withdrawn to enable a patient to ventilate himself in a normal, natural manner spontaneously through the nose and mouth. According to the present invention there is provided a tracheotomy tube having a cuffed end with an aperture or opening in the wall of the tube intermediate its ends and means slidably cooperable with the wall of the tube to selectively open and close the aperture or opening therein, said means being such as to provide a minimum change in the bore of the tube.

Conveniently, the tube can be provided with first and second removable inserts. The first insert is adapted to sealingly close the aperture when a patient is connected to a ventilator. The second insert is adapted to expose the aperture while providing a support for the wall of the tube in the region of the aperture when the patient is ventilating himself in a normal, natural manner.

BRIEF DESCRIPTION OF THE DRAWINGS

The invention will now be described, by way of example, with reference to the accompanying drawings; in which:

FIG. 1 is an exploded diagrammatic view of one embodiment of a tube and insert;

FIG. 2 is a plan view of an insert,

FIG. 3 is a section, not to scale, of an end of the tube and a connector for a ventilator, and FIG. 4 is a diagrammatic section of an alternative embodiment of a tube and insert.

DETAILED DESCRIPTION

A tracheotomy tube according to the invention comprises a cuffed and fenestrated tube 1 and a removable insert 2 cooperable with the tube 1 in a manner to be described.

The tube 1 is substantially identical to existing known tubes except that it is provided with an opening or aperture 3 which is positioned to enable the interior of the tube to communicate with the windpipe. The tube is conveniently formed from a plastics material but the tube can be a metal. A cuff 4 at or adjacent the leading end of the tube can be inflated from an external pump, through a narrow passage 5 formed in the wall of the tube. At its opposite end the tube is provided with a connection piece 6 for connection to a ventilator and a collar or wing 7 to receive anchoring tabs or tapes for securing about the neck of a patient.

When the tube is fitted in position within the patient the cuff is inflated to provide an airtight seal between the tube and the wall of the windpipe and a ventilator is connected to the connection piece to ventilate the patient.

Clearly with the apertured or fenestrated tube most if not all of the output of the ventilator will exhaust through the aperture 3. Consequently means are required to close and seal the aperture 3. Such a means comprises the removable insert 2 having substantially the same radius of curvature as the tube 1 and which can readily be inserted into and withdrawn from the tube.

It is essential to maintain the bore of the tube 1 as unobstructed as possible in order to avoid unnecessary reduction of its cross-section. This is required to enable a catheter or the like to be inserted into the tube with the minimum of difficulty. The design and configuration of the insert 2 is such as to achieve the above requirements.

In any plane taken normal to its length the insert 2 is of part annular section and preferably not greater than a semi-circle. The insert 2 can be imagined as a thin walled tube, conveniently formed from a plastic or metal, having an outside diameter equal to the internal diameter of the tube 1 and curved to fit the internal configuration of the tube. Three axially extending cut-out portions are formed in the tube wall of the insert. A first cut-out portion 8 is provided at the leading end of the insert and this portion extends beyond the leading end of the aperture 3. This first cut-out portion is formed in the lower half of the insert and the upper half forms a sealing surface 9 engageable in the aperture. A second cut-out portion 10 extends from adjacent the first cut-out portion to the end of the insert adapted to engage the ventilator connection. This second portion is likewise formed in the lower half of the insert and is separated from the first portion by a bridge piece 11. A third cut-out portion 12 is formed in the upper half of the insert and the opposite ends of this third portion overlap the adjacent ends of the first and second cut-out portions.

The sealing surface 9 is profiled and contoured to form a raised button or bulbous portion which fits into the aperture 3 in the tube 1. The leading edge 13 of the button has a sharp or abrupt profile which cooperates with the leading end of the aperture in the tube 1 to locate the insert in its operative position within the tube. On the other hand the trailing edge of the button is formed with a gradual smooth profile which engages the trailing end of the aperture in the tube and allows easy withdrawal of the insert from the tube. The design of the insert is such as to provide three point pressure application within the tube 1 which operates to urge the button into the aperture 3 in the tube. To ensure that the raised button is urged into engagement with the rim of the aperture it is desirable to locate the bridge piece 11 rearwardly of the centre of length of the insert. The trailing end of the insert can be provided with a key or spline 14 engageable in a corresponding slot 15 or the like in the end of the tube for locking the insert against rotation. The insert terminates in an integral annular collar 16.

When the insert 2 is inserted into the tube 1 to seal closed the aperture 3 the tube functions in the manner of a conventional tracheotomy tube and the patient is ventilated by connecting the tube to a ventilator. When it is required to wean the patient off the ventilator, the ventilator is disconnected from the tube and the insert can be removed to expose the aperture in the tube which remains in position within the windpipe. With the aperture open the patient is encouraged to ventilate himself in a normal manner through the nose and mouth while at the same time it is possible, if required, to supply the patient with oxygen through the tube externally. Initially the insert will only be withdrawn for a short period before the patient is again reconnected to the ventilator. Subsequently, as the patient improves and gains confidence the periods of withdrawal of the insert can be progressively increased until the patient can ventilate himself adequately without assistance. The tube 1 can remain in position at all times thus avoiding the discomfort and distress to the patient that can result from its repeated withdrawal and re-insertion.

The insert can be formed from a material capable of being sterilised in an autoclave and conveniently a plurality of inserts can be provided for use with each tube. Alternatively the insert can be disposed of after use.

It is possible that the tube can deform or partially collapse in the region of the aperture. As mentioned above it is necessary to maintain the cross-section of the tube as open as possible in order to ensure adequate ventilation and to avoid undue difficulty in the insertion and withdrawal of a catheter. Consequently, the tube can be provided with a second separate insert of the same general shape and configuration as the above mentioned first insert but having an aperture, corresponding to the aperture in the tube, in its upper surface 9. In effect the aperture in the second insert replaces the button or bulbous portion of the first insert. Such an insert when entered into the tube during the intervals when the patient is being encouraged to ventilate naturally will serve to maintain the desired cross-sectional configuration of the aperture in the tube.

It will be appreciated that the manner and type of connections to the ventilator and any supplemented supply of oxygen can be a matter of choice and that such connections can, if required, be formed integral with the inserts.

One possible form of connection is shown in FIG. 3. A connector 17 is a push fit on to the end 6 of the tube and has a rotatable sleeve 18 which cooperates with a rotatable collar 19 on the tube in order that the connector can be rotated relative to the tube. The insert is located in position within the tube and the annular collar is retained between the end of the tube and a stepped portion of the connector. A port 20 leads to a ventilator and a second port 21 is provided with a removable plug 22. This plug can be removed for the insertion of a catheter. The insert 2 is secured and urged into its correct position to close the aperture by means of the connector 17 engaging the annular collar 16 and the key engaging in the slot in the end of the tube prevents relative rotation between the tube and the insert.

In an alternative embodiment, the insert means can comprise a strip of resiliently flexible material, such as a plastics material, and the tube can be provided with guideways extending lengthwise along the tube from a position at or adjacent the ventilator connection to a position at the forward end of the aperture in the tube. The lateral spacing of the guideways is such that the insertable strip is a sliding fit therein with the guideways urging the strip into engagement with the surface of the tube. Preferably a lateral stop is arranged at the ends of the guideways adjacent the forward end of the aperture which is directed towards the cuffed end of the tube. This stop, which can join the ends of the guideways, is provided with a lip which is adapted to co-operate with the leading end of the insertable strip to urge the leading end into engagement with the tube. This provides a close fit of the insertable strip about the aperture. Such an arrangement as illustrated diagrammatically in FIG. 4 which is a section through a fenestrated tracheotomy tube 40. Reference numerals 41, 42 and 43 respectively indicate the guideways, stop and slidable strip and numeral 44 indicates the aperture in the wall of the tube.

The tracheotomy tube is generally formed from a plastics material and the guideways and end stop can be formed from the same or a similar plastics material which can be welded, fused or adhered to the tube. Conveniently it is envisaged that the guideways and end stop can be formed as an integral unit in the form of a channel with the base of the channel having a shape and curvature conforming to the shape and curvature of the tracheotomy tube. A portion of the tracheotomy tube, corresponding in size to the size of the channel can be removed and replaced by the channel which can be fused, welded, adhered or otherwise secured to the tube. The aperture which is to be opened and closed by the insertable strip is now formed in the base of the channel.

The channel can be arranged and positioned such that the guideways and end stop are disposed on the external or internal surface of the tube. Preferably, the guideways and end stop are arranged internally of the tube so as to ensure a smooth, uninterrupted external tube surface. This results in the minimum of discomfort to the patient during insertion and removal of the tracheotomy tube.

As an alternative to a tube with depending guideways a slot to receive the insertable strip can be formed in the wall of the tube.

I claim:

1. A tracheotomy tube having a cuffed end with an aperture in the wall of the tube intermediate its ends and means slidably cooperable with the wall of the tube to selectively open and close the aperture therein, said means being such as to provide a minimum change and obstruction in the bore of the tube, said means comprising a removable insert slidable in the bore of the tube, the insert having substantially the same curvature as the tube and having a sealing surface adapted to cooperate with the aperture in the wall of the tube, and the removable insert comprising a thin wall tubular body having three axially extending cut-out portions such that in any plane normal to its length the insert is of part-annular section, a first and second of said cut-out portions being separated by a bridge piece formed in a lower portion of the insert remote from the sealing surface, and the third cut-out portion being formed in the upper portion of the insert and overlapping the adjacent ends of the first and second cut-out portions.

2. A tracheotomy tube according to claim 1 in which the sealing surface is profiled and contoured to form a raised portion which fits into the aperture in the wall of the tube.

3. In combination, a tracheotomy tube and removable insert means, the tube having an inflatable cuffed end for insertion in a patient's trachea, an opposite end for releasable connection to a ventilator and an aperture in the wall of the tube intermediate its ends, the removable insert means cooperating with the tube to engage and seal the aperture in an airtight fit, said insert means being such as to provide a minimum change and obstruction in the bore of the tube whereby, in use, with the cuff inflated and said insert means in sealing engagement with the aperture a patient can be ventilated by the ventilator and upon removal of the insert means the patient can breathe spontaneously through the nose and mouth.

4. A combination according to claim 3, in which the insert means is formed with a sealing surface which is profiled and contoured to sealingly engage the aperture in the tube, the insert means being cooperable with the tube to continually urge the sealing surface into sealing engagement with the aperture.

5. A combination according to claim 4, including cooperable keying means on the tube and the insert means to prevent relative rotational movement therebetween when the insert means is located in the tube in sealing engagement with the aperture.

6. A combination according to claim 3, in which the insert means comprises a thin wall tubular body having three axially extending cut-out portions such that in any plane normal to its length the insert means is of part-annular section, a first and second of said cut-out portions being separated by a bridge piece formed in a lower portion of the insert means remote from the sealing surface, and the third cut-out portion being formed in the upper portion of the insert means and overlapping the adjacent ends of the first and second cut-out portions.

7. A combination according to claim 3, in which the insert means comprises an elongated insert member which is slidably positionable within the interior bore of the tube so that the insert member slidably engages only the upper internal wall of the interior bore, said insert member having a sealing portion which is profiled and contoured to sealingly engage the aperture in the tube when the insert member is positioned within the tube.

8. A combination according to claim 7, wherein the insert member continuously urges the sealing portion into sealing engagement with the aperture so as to close same when the insert member is properly positioned within the tube.

9. A combination according to claim 8, wherein the sealing portion of the insert member forms a raised or bulbous portion which fits into the aperture for sealingly closing same.

* * * * *